United States Patent
Eyal

(10) Patent No.: US 10,617,722 B2
(45) Date of Patent: Apr. 14, 2020

(54) HONEY-CANNABINOID THERAPEUTIC COMPOSITION

(71) Applicant: Canna-B Cure Ltd, Or-Akiva (IL)

(72) Inventor: Aharon M. Eyal, Jerusalem (IL)

(73) Assignee: CANNA-B CURE LTD, Or-Akiva (IL)

( * ) Notice: Subject to any disclaimer, the term of this patent is extended or adjusted under 35 U.S.C. 154(b) by 0 days.

(21) Appl. No.: 15/771,908

(22) PCT Filed: Oct. 27, 2016

(86) PCT No.: PCT/IB2016/056489
§ 371 (c)(1),
(2) Date: Apr. 27, 2018

(87) PCT Pub. No.: WO2017/072704
PCT Pub. Date: May 4, 2017

(65) Prior Publication Data
US 2018/0318361 A1   Nov. 8, 2018

Related U.S. Application Data

(60) Provisional application No. 62/249,206, filed on Oct. 31, 2015.

(51) Int. Cl.
| | | |
|---|---|---|
| A61K 36/18 | (2006.01) |
| A61K 35/644 | (2015.01) |
| A61K 31/352 | (2006.01) |
| A23L 21/25 | (2016.01) |
| A23L 21/00 | (2016.01) |
| A61K 36/185 | (2006.01) |
| A61K 31/05 | (2006.01) |
| A61K 45/06 | (2006.01) |
| A23L 33/105 | (2016.01) |
| A61K 9/00 | (2006.01) |
| A61K 38/44 | (2006.01) |

(52) U.S. Cl.
CPC ............ *A61K 35/644* (2013.01); *A23L 21/00* (2016.08); *A23L 21/25* (2016.08); *A23L 33/105* (2016.08); *A61K 9/0014* (2013.01); *A61K 9/0056* (2013.01); *A61K 31/05* (2013.01); *A61K 31/352* (2013.01); *A61K 36/185* (2013.01); *A61K 38/443* (2013.01); *A61K 45/06* (2013.01); *A23V 2002/00* (2013.01); *A61K 2236/00* (2013.01); *A61K 2300/00* (2013.01); *C12Y 101/03004* (2013.01)

(58) Field of Classification Search
CPC ....................................................... A61K 36/18
See application file for complete search history.

(56) References Cited

U.S. PATENT DOCUMENTS

| 8,445,034 B1 | 5/2013 | Coles, Jr. |
| 2006/0160888 A1 | 7/2006 | Kottayil et al. |

FOREIGN PATENT DOCUMENTS

| WO | 2015/068052 | 5/2015 | |
| WO | WO-2015117011 A1 * | 8/2015 | ............. A61K 36/82 |

OTHER PUBLICATIONS

Google Patents translation of Lu, CN 103222646 A, 2013.*
Google Patents translation of Anlain, CN 101167832 B, 2012.*
Official Communication issued in International Bureau of WIPO Patent Application No. PCT/IB2016/056489, dated Mar. 23, 2017.

* cited by examiner

*Primary Examiner* — Rosanne Kosson
(74) *Attorney, Agent, or Firm* — Eva Taksel

(57) ABSTRACT

Honey-cannabinoid therapeutic compositions and methods. A therapeutic composition providing therapeutic effects to at least some patients is described including honey; at least one cannabinoid; and optionally, at least two non-cannabinoid cannabis compounds, hydrogen peroxide, at least one food-approved antioxidant, glucose oxidase, and/or catalase, and water; where the composition is homogeneous; has oxidative power low enough to keep tetrahydrocannabinol oxidation at a rate of less than 20% per month; contains hydrogen peroxide at a concentration low enough to keep tetrahydrocannabinol oxidation at a rate of less than 20% per month; contains at least one food-approved antioxidant at a concentration low enough to keep THC oxidation at a rate of less than 20% per month; contains glucose oxidase at a concentration low enough to keep tetrahydrocannabinol oxidation at a rate of less than 20% per month; and/or contains catalase at a concentration high enough to keep tetrahydrocannabinol oxidation at a rate of less than 20% per month.

13 Claims, No Drawings

HONEY-CANNABINOID THERAPEUTIC COMPOSITION

CROSS-REFERENCE TO RELATED APPLICATIONS

The present application claims the benefit of U.S. Provisional Application Ser. No. 62/249,206 filed Oct. 31, 2015, the disclosure of which is expressly incorporated by reference herein in its entirety.

BACKGROUND

Cannabis extract is known to have therapeutic effects. Those effects depend on the extract composition, including the content and nature of various cannabinoids and possibly also on the content of non-cannabinoid cannabis components, such as terpenes. Cannabis therapeutic effects are, in many cases, personal and can change from one patients to the other. Honey is known to have therapeutic effects. There is a need for greater and additional therapeutic effects. Combining honey with cannabis active components faces challenges, such as instable and inconsistent compositions, which as such are unsuitable for use as therapeutic compositions.

SUMMARY OF THE INVENTION

A therapeutic composition providing therapeutic effects to at least some patients is described including honey; at least one cannabinoid; and optionally, at least two non-cannabinoid cannabis compounds, hydrogen peroxide, at least one food-approved antioxidant, glucose oxidase, and/or catalase, and water at a concentration of less than 26% wt; where the composition is characterized by one or more of being homogeneous; having oxidative power low enough to keep tetrahydrocannabinol oxidation at a rate of less than 20% per month; containing hydrogen peroxide at a concentration low enough to keep tetrahydrocannabinol oxidation at a rate of less than 20% per month; containing at least one food-approved antioxidant at a concentration low enough to keep THC oxidation at a rate of less than 20% per month; containing glucose oxidase at a concentration low enough to keep tetrahydrocannabinol oxidation at a rate of less than 20% per month; and/or containing catalase at a concentration high enough to keep tetrahydrocannabinol oxidation at a rate of less than 20% per month.

Additional embodiments include: the therapeutic composition described above, additionally characterized by at least two of (a) to (f); the therapeutic composition described above, additionally characterized by at least three of (a) to (f); the therapeutic composition described above, additionally characterized by at least four of (a) to (f); the therapeutic composition described above, additionally characterized by (a) and at least one of (b) to (f); the therapeutic composition described above, where said cannabinoid is selected from the group consisting of tetrahydrocannabinol, cannabidiol and combinations thereof; the therapeutic composition described above, containing at least two non-cannabinoid cannabis compounds, wherein at least one of said non-cannabinoid cannabis compound is selected from the group consisting of terpenes, terpenoids and flavonoids; the therapeutic composition described above, wherein the concentration of cannabinoid in the composition is less than 10% by weight; the therapeutic composition described above, wherein the concentration of cannabinoid in the composition is greater than 10 parts per million of total component parts present in the composition; the therapeutic composition described above, wherein said cannabinoid comprises cannabidiol and tetrahydrocannabinol in a weight ratio of cannabidiol to tetrahydrocannabinol greater than 5; the therapeutic composition described above, where at least one therapeutic effect provided to at least some patients is greater than that provided by the at least one cannabinoid; the therapeutic composition described above wherein at least one therapeutic effect provided to at least some patients is in addition to the therapeutic effects provided by the at least one cannabinoid and honey; a digestible product containing the therapeutic composition described above; and a topical application product containing the therapeutic composition described above.

A method of producing a therapeutic composition is also described including providing honey; providing a cannabis extract comprising cannabinoid and non-cannabinoid cannabis compounds; and blending said provided honey and said provided cannabis extract to form a blend Additional embodiments include: the method described above, including homogenizing the blended components; the method described above, where the blending is conducted at a temperature below 90° C.; the method described above, where the blending is conducted at a temperature above 30° C.; the method described above, where the cannabinoid is provided as a cannabis extract comprising a solvent, and at least a fraction of said solvent is removed during blending, after blending, or in a combination thereof; the method described above where the cannabis extract is produced by the extraction of cannabis plant material; the method described above where the cannabis extract is enriched in the cannabinoid; the method described above where a cannabis extract is provided by enrichment in at least one non-cannabinoid cannabis compound; the method described above where the honey comprises glucose oxidase and the method further comprises at least partially deactivating and/or denaturing said glucose oxidase prior to said blending or simultaneously therewith.

DETAILED DESCRIPTION OF THE INVENTION

Provided is a composition providing therapeutic effects to at least some patients comprising, (i) honey; (ii) at least one cannabinoid; and (iii) optionally, at least two non-cannabinoid cannabis compounds, hydrogen peroxide, at least one food-approved antioxidant, glucose oxidase, and/or catalase, and (iv) water at a concentration of less than 26% wt; wherein the composition is characterized by one or more of (a) being homogeneous; (b) having oxidative power low enough to keep tetrahydrocannabinol oxidation at a rate of less than 20% per month; (c) containing hydrogen peroxide at a concentration low enough to keep tetrahydrocannabinol oxidation at a rate of less than 20% per month; (d) containing at least one food-approved antioxidant at a concentration low enough to keep tetrahydrocannabinol oxidation at a rate of less than 20% per month; (e) containing glucose oxidase at a concentration low enough to keep tetrahydrocannabinol oxidation at a rate of less than 20% per month; and/or (f) containing catalase at a concentration high enough to keep tetrahydrocannabinol oxidation at a rate of less than 20% per month. According to various embodiments, the composition is characterized by at least two of (a) to (f), at least three or at least four. According to an embodiment the composition is characterized by (a) and at least one of (b) to (f).

According to an embodiment, said cannabinoid is selected from the group consisting of tetrahydrocannabinol, cannabidiol and combinations thereof. According to another embodiment, said cannabinoid comprises cannabidiol and tetrahydrocannabinol in a weight ratio of cannabidiol to tetrahydrocannabinol greater than 5.

According to an embodiment, said composition contains at least two non-cannabinoid cannabis compounds, wherein at least one of said non-cannabinoid cannabis compound is selected from the group consisting of terpenes, terpenoids and flavonoids.

According to various embodiments, the concentration of cannabinoid in the composition is less than 10% by weight; and the concentration of cannabinoid in the composition is greater than 10 parts per million of total component parts present in the composition.

According to various embodiments, at least one therapeutic effect provided to at least some patients is greater than that provided by the at least one cannabinoid and at least one therapeutic effect provided to at least some patients is in addition to the therapeutic effects provided by the at least one cannabinoid and honey.

According to various embodiments, further provided are digestible product containing said composition and a topical application product containing that composition.

According to an embodiment, further provided is a method of producing a therapeutic composition comprising providing honey; providing a cannabis extract comprising said cannabinoid and said non-cannabinoid cannabis compounds; and blending said provided honey and said provided cannabis extract to form a blend. According to another embodiment, said method further comprises homogenizing the blended components.

According to various embodiments, said blending is conducted at a temperature below 90° C. and said blending is conducted at a temperature above 30° C.

According to an embodiment, said cannabinoid is provided as a cannabis extract comprising a solvent, and at least a fraction of said solvent is removed during blending, after blending, or in a combination thereof.

According to various embodiments, said cannabis extract is produced by the extraction of cannabis plant material; said cannabis extract is enriched in the cannabinoid and a cannabis extract is provided by enrichment in at least one non-cannabinoid cannabis compound According to an embodiment, said honey comprises glucose oxidase and said method further comprises at least partially deactivating and/or denaturing said glucose oxidase prior to said blending or simultaneously therewith.

Definitions

Unless specified otherwise, all concentrations are weight concentrations and all ratios are weight per weight (weight/weight) ratios.

As used herein, water content refers to total water content, e.g. water resulting from any source, including water in the honey fraction.

The term cannabinoid(s) refers to both cannabinoid(s) in carboxylic acid form and cannabinoid(s) in decarboxylated form.

Unless specified otherwise, the term tetrahydrocannabinol refers to both its carboxylic acid form and its decarboxylated from, which are also referred to as THC.

Unless specified otherwise, the term cannabidiol refers to both its carboxylic acid form and its decarboxylated from, which are also referred to as CBD.

As used herein, the term non-cannabinoid cannabis compound means a non-cannabinoid compound present in at least one strain of cannabis plants.

As used herein, the term terpene refers to compounds comprising at least one isoprene unit. As used herein the terms terpene and terpenoid are used herein interchangeably.

As used herein the term honey refers to concentrated sugar compositions referred to commercially as honey and excludes cannabis extract as such. Compositions according to the present invention may comprise a blend of honey and a cannabis extract.

As used herein, the terms "homogeneous" and "of consistent composition" are interchangeable.

As used herein, the term a composition comprising honey refers to a composition comprising components of commercial pure honey (sugars, amino acids, organic acids, furfurals, vitamins, minerals) at concentrations of at least 90% of their concentrations in commercial pure honey.

As used herein, the term commercial pure honey refers to unadulterated honey sold globally at a rate of at least one ton per year.

As used herein the term molecularly distributed means in contact with other composition components as in theoretical solution or present in micro-phases of less than 1 micron.

As used herein the term effect applies to any of a single effect, multiple effects and a combination of effects.

As used herein, unless specified otherwise, the terms preparation(s), other preparation(s) and another preparation refer to cannabinoids-comprising compositions other than those of the present invention.

Provided is a composition providing therapeutic effects to at least some patients comprising, (i) honey; (ii) at least one cannabinoid; and (iii) optionally, at least two non-cannabinoid cannabis compounds, hydrogen peroxide, at least one food-approved antioxidant, glucose oxidase, and/or catalase, and (iv) water at a concentration of less than 26% wt; wherein the composition is characterized by one or more of (a) being homogeneous; (b) having oxidative power low enough to keep tetrahydrocannabinol oxidation at a rate of less than 20% per month, less than 15%, less than 10%, less than 5% or less than 2%; (c) containing hydrogen peroxide at a concentration low enough to keep tetrahydrocannabinol oxidation at a rate of less than 20% per month, less than 15%, less than 10%, less than 5% or less than 2%; (d) containing at least one food-approved antioxidant at a concentration low enough to keep tetrahydrocannabinol oxidation at a rate of less than 20% per month, less than 15%, less than 10%, less than 5% or less than 2%; (e) containing glucose oxidase at a concentration low enough to keep tetrahydrocannabinol oxidation at a rate of less than 20% per month, less than 15%, less than 10%, less than 5% or less than 2%; and/or (f) containing catalase at a concentration high enough to keep tetrahydrocannabinol oxidation at a rate of less than 20% per month, less than 15%, less than 10%, less than 5% or less than 2%. According to various embodiments, the composition is characterized by at least two of (a) to (f), at least three, at least four, at least five or all six. According to an embodiment the composition is characterized by (a) and at least one of (b) to (t), at least two, at least three, at least four or all five.

According to an embodiment, said honey is selected from bees honey and date honey. Since said composition comprises other components besides honey, it is not honey, but has a composition similar to that of honey. Hence, according to an embodiment, it comprises components of commercial pure honey (e.g. sugars, amino acids, organic acids, furfurals, vitamins, minerals) at concentrations of at least 90% of their concentrations in commercial pure honey. For example, the study summarized in http://www.inframiel.ch/ATR_Quant.pdf, presenting the analysis of more than 100 samples of bees' honey, found mean concentrations of fructose, glucose and total sugars of 38.3% wt, 29.4% wt and 78.4% wt, respectively. Accordingly, as used herein, a composition comprising honey may comprise at least 34.5% wt fructose, at least 26.5% glucose and at least 70.6% total sugars. According to another embodiment, said honey-comprising composition comprises honey sugars at ratios similar to those in commercial pure honey (e.g. fructose/glucose weight/weight ratios of about 1.3) or sugars/water weight/weight ratios similar to those in commercial pure honey (e.g. glucose/water weight/weight ratio of about 1.9). See also Escuredo et. al., Food Chemistry 138 (2013) 851-856. Any analytical method is suitable, e.g. that of the Association of Official Analytical Chemists and isotope analysis.

Bees honey compositions depend on the composition of nectar used to form the honey. Bees honeys contain components characteristic to the flowers foraged. According to an embodiment, said therapeutic composition comprises components characteristic to eucalyptus honey, avocado honey, orange blossom honey or Manuka honey.

According to an embodiment, total sugars concentration in said therapeutic composition is at least 72% wt, at least 74% wt, at least 76% wt, at least 78% wt, at least 80% wt or at least 82% wt.

According to an embodiment, said therapeutic composition comprises wax and wax concentration there is less than 0.3%, less than 0.2%, less than 0.1%, less than 0.08%, less than 0.06%, less than 0.04%, less than 0.02% or less than 0.01%.

According to an embodiment, said therapeutic composition comprises chlorophyll and chlorophyll concentration there is less than 0.3%, less than 0.2%, less than 0.1%, less than 0.08%, less than 0.06%, less than 0.04%, less than 0.02% or less than 0.01%.

According to an embodiment, said cannabinoid is selected from the group consisting of THC, CBD and a combination thereof. According to an embodiment, said cannabinoid is THC. According to an embodiment, said cannabinoid is CBD. According to an embodiment, said cannabinoid is in its decarboxylated form. According to an embodiment, said therapeutic composition comprises at least two cannabinoids, at least three cannabinoids or at least four cannabinoids.

According to an embodiment, said therapeutic composition comprises both CBD and THC at CBD to THC weight/weight ratio greater than 5, greater than 10, greater than 15, greater than 20 or greater than 30. According to another embodiment, said therapeutic composition comprises both CBD and THC at THC to CBD weight/weight ratio greater than 5, greater than 10, greater than 15, greater than 20 or greater than 30.

According to an embodiment, cannabinoid concentration in said therapeutic composition is less than 10% wt, less than 5% wt, less than 2% wt, less than 1% wt, less than 5000 ppm, less than 2000 ppm, or less than 1000 ppm.

According to an embodiment, cannabinoid concentration in said therapeutic composition is greater than 10 ppm, greater than 50 ppm, greater than 100 ppm, greater than 200 ppm, greater than 300 ppm, greater than 300 ppm, greater than 500 ppm, greater than 600 ppm, greater than 700 ppm, greater than 800 ppm, greater than 900 ppm, greater than 1000 ppm, greater than 1200 ppm, greater than 1400 ppm, greater than 1600 ppm, greater than 1800 ppm or greater than 2000 ppm.

According to an embodiment, said therapeutic composition comprises at least two non-cannabinoid cannabis compounds, at least 5, at least 10 or at least 15. According to an embodiment, at least one of said non-cannabinoid cannabis compounds is selected from the group consisting of terpenes, terpenoids and flavonoids. According to an embodiment, at least one of said non-cannabinoid cannabis compounds is selected from the group consisting of pinenes, limonene, linalool, caryophyllene, myrcene, humulene, borneol, eucalyptol, terpineol and combinations thereof.

According to an embodiment, the weight/weight ratio between the amount of said at least one cannabinoid in said therapeutic composition and the total amount of said non-cannabinoid cannabis compounds in said therapeutic composition is greater than 1, greater than 2, greater than 5, greater than 10, greater than 20, or greater than 30.

According to an embodiment, said therapeutic composition comprises a solvent.

According to an embodiment, said therapeutic composition comprises at least one lipid-soluble compound, e.g. a vitamin, vegetable oil, an antioxidant and/or an essential oil. According to an embodiment, said therapeutic composition comprises at least one lipid-soluble compound at a concentration greater than 100 ppm, greater than 500 ppm greater than 1000 ppm, greater than 5000 ppm, greater than 1% wt, or greater than 2% wt. According to an embodiment, said therapeutic composition comprises at least one vegetable oil. According to an embodiment, said therapeutic composition comprises at least one food-approved emulsifier. According to an embodiment, said therapeutic composition comprises at least 10 ppm vitamin E. According to an embodiment, said therapeutic composition comprises at least one flavoring agent. According to an embodiment, said therapeutic composition comprises at least one essential oil.

According to an embodiment, said therapeutic composition comprises less than 40 wt % water, less than 38 wt %, less than 36% wt, less than 34% wt, less than 32% wt, less than 30% wt, less than 28% wt, less than 26% wt %, less than 25 wt %, less than 24% wt, less than 23% wt, less than 22% wt, less than 21% wt, less than 20% wt, less than 19 wt %, less than 18% wt, less than 17% wt, less than 16% wt, less than 15% wt, less than 14% wt, less than 13% wt, less than 12% wt, less than 11% wt or less than 10% wt.

A key requirement for medical cannabis compositions is an accurate and a repeatable composition, ensuring that the patient receives in each treatment the prescribed amount of active components. Mixing honey with cannabis plant extracts results many times in disappointing results. For example, several types of honey were mixed, as such or after some water addition, with cannabis extracts, e.g. ones from various cannabis strains and ones extracted with various extractants. Cannabinoids concentrations in the extracts were analyzed prior to mixing. Those concentrations and the honey/extract mixing ratios were used to calculate the predicted cannabinoids concentrations in the formed mixtures. Analysis of the mixtures, at various times after mixing, showed in many cases, results that are markedly different from the calculated ones. In many cases, the actual concentrations were several times lower than the calculated ones.

Cannabinoids are of low polarity. THC, for example, has the formula of $C_{21}H_{30}O_2$, i.e. C/O molar ratio of 10.5/1, which explains its low solubility in water—0.0028 gr/L. Honey, on the other hand, contains nearly 80% sugars (C/O molar ratio of about 1/1) and mixes perfectly with water. It was surprisingly found that homogeneous therapeutic blends of cannabinoids with honey are attainable and that those compositions are stable in maintaining consistent composition over weeks and months.

According to an embodiment, said therapeutic composition is characterized by being homogenous or of consistent composition. As used herein, homogeneous means consistent distribution of said at least one cannabinoid. According to an embodiment, at least two samples of at least about 500 mg each, taken from said therapeutic composition have similar concentrations of said at least one cannabinoid, e.g. within 10% difference. According to an embodiment, at least 10% of the cannabinoid in said therapeutic composition is molecularly distributed in said therapeutic composition, at least 20%, at least 30%, at least 40%, or at least 50%.

According to an embodiment, at least two samples of at least about 500 mg each, taken from therapeutic composition comprising multiple cannabinoids, have similar concentrations of multiple (e.g. at least 2, at least 3, at least 5 or at least 10) cannabinoid, e.g. within 10% difference (e.g. in case said therapeutic composition comprises cannabinoid A and cannabinoid B, the concentration of cannabinoid A in one sample is similar to the concentration of cannabinoid A in another sample and the concentration of cannabinoid B in one sample is similar to the concentration of cannabinoid B in another sample). According to an embodiment, at least 10% of multiple (e.g. at least 2, at least 3, at least 5 or at least 10) cannabinoids in said therapeutic composition are molecularly distributed in said therapeutic composition, at least 20%, at least 30%, at least 40%, or at least 50%.

According to an embodiment, said therapeutic composition is further characterized by homogeneous or consistent distribution of at least one non-cannabinoid cannabis compounds. According to an embodiment, at least two samples, of at least about 500 mg each, taken from said therapeutic composition have similar concentrations of said at least one non-cannabinoid cannabis compounds, e.g. within 10% difference. According to an embodiment, at least two samples, of at least about 500 mg each, taken from said therapeutic composition have similar concentrations of multiple (e.g. at least 2, at least 3, at least 5 or at least 10) non-cannabinoid cannabis compounds, e.g. within 10% difference. According to an embodiment, at least 10% of multiple (e.g. at least 2, at least 3, at least 5 or at least 10) non-cannabinoid cannabis compounds in said therapeutic composition are molecularly distributed, at least 20%, at least 30%, at least 40%, or at least 50%.

It was also found that homogeneous therapeutic compositions of cannabinoids with honey, where oxidative power is reduced, are stable. According to an embodiment, the therapeutic composition is characterized by oxidative power low enough to keep THC oxidation at a rate of less than 20% per month. Without wishing to be limited by theory, it is possible that at least part of the discovered therapeutic composition instability is due to oxidation of cannabinoids by oxidants present and/or formed in honey, e.g. hydrogen peroxide and/or oxygen. Possibly, the relative rate of said oxidation increases with the decrease in cannabinoid concentration and with increased homogeneity of the composition, which improves cannabinoids contact with the oxidizing agent.

Studies of honey antimicrobial activity deal with hydrogen peroxide generation and content in honey, e.g. the critical review Antibacterial Components of Honey, by Kwakman and Zaat in IUBMB Life 64 (2012) 48-55. Various honeys contain hydrogen peroxide. Hydrogen peroxide concentrations in honey vary significantly between honeys from various sources. It is suggested there that Hydrogen peroxide in honey results from glucose-oxidase-catalyzed conversion of glucose in aerobic conditions into gluconic acid and hydrogen peroxide. Glucose oxidase activity increases on dilution of pure honey, reaching a maximum at about 30-50% concentration of honey.

Oxidative power of honey is difficult to conclude from analysis of contained oxidants. One reason for that is that honey is a highly concentrated solution of sugars (supersaturated according to some studies), where water activity is very low. This has a drastic affect on the activity of other solutes. Water activity is also affected by moisture absorption from the environment since honey is highly hygroscopic. Oxygen content in the honey also plays a role and possibly also temperature and light irradiation. Also important are the concentration of glucose oxidase and the parameters affecting its activity. The same could be true for enzymes catalyzing degradation of hydrogen peroxide, e.g. catalase, if present. pH may also play a role (honey is typically slightly acidic). Also important are the concentration and activity of other components of the composition, e.g. ones acting as antioxidants.

An indirect method of determining the oxidative power of a given therapeutic composition is testing THC oxidation rate in it. According to a suitable testing protocol, about 2 gr of an extract comprising at least 60% wt THC are thoroughly mixed with about 100 gr of the composition to be tested. Three samples of about 500 mg are taken right after mixing and analyzed in order to determine the actual initial THC concentration in the mixture. Two days later, three additional samples of about 500 mg are taken and analyzed. Sampling and analysis is repeated every 2-3 days for a total of about two weeks. In all cases, analysis is conducted shortly after sampling. Drop in THC concentration is plotted and extrapolated for a full month (here, 30 days). According to this protocol, this drop is assigned to THC oxidation.

Similar testing protocols can be used for determining the effect on THC oxidation of individual parameters, such as concentrations of hydrogen peroxide, oxygen, antioxidant, glucose oxidase, catalase and water.

According to an embodiment, the therapeutic composition is characterized by oxidative power low enough to keep THC oxidation at a rate of less than 20% per month, less than 15%, less than 10%, less than 5% or less than 2%. According to another embodiment, the therapeutic composition comprises hydrogen peroxide and is characterized by hydrogen peroxide concentration low enough to keep THC oxidation at a rate of less than 20% per month, less than 15%, less than 10%, less than 5% or less than 2%. According to another embodiment, the therapeutic composition comprises oxygen and is characterized by oxygen concentration low enough to keep THC oxidation at a rate of less than 20% per month, less than 15%, less than 10%, less than 5% or less than 2%. According to another embodiment, the therapeutic composition comprises at least one food-approved antioxidant and is characterized by antioxidant concentration high enough to keep THC oxidation at a rate of less than 20% per month less than 15%, less than 10%, less than 5% or less than 2%. According to an embodiment, According to various embodiments said antioxidant comprises antioxidants naturally present in commercial honey (See also Escuredo et. al., Food Chemistry 138 (2013) 851-856.) and/or other ones. According to an embodiment, said antioxidant comprises tocopherol. According to another embodiment, the therapeutic composition comprises glucose oxidase and is characterized by glucose oxidase concentration low enough to keep THC oxidation at a rate of less than 20% per month, less than 15%, less than 10%, less than 5% or less than 2%.

According to another embodiment, the therapeutic composition comprises catalase and is characterized by catalase concentration high enough to keep THC oxidation at a rate of less than 20% per month, less than 15%, less than 10%, less than 5% or less than 2%. According to another embodiment, the therapeutic composition comprises water and is characterized by water concentration low enough to keep THC oxidation at a rate of less than 20% per month, less than 15%, less than 10%, less than 5% or less than 2%.

According to an embodiment, at least one therapeutic effect provided to at least some patients by said therapeutic composition is greater than that provided by the at least one cannabinoid. According to an embodiment, said therapeutic effect is greater than the effect of said cannabinoid in a preparation other than said therapeutic composition, e.g. an extract, which other preparation contains same cannabinoid at same amount.

Pain relief of a therapeutic composition according to the present invention, which composition comprises 2 mg THC, can be compared with that of THC-containing extract diluted with olive oil. According to an embodiment, for at least some patients, pain relief with the therapeutic composition is greater than that found when using oil-dilutes extract containing 2 mg THC, 3 mg THC, 4 mg THC, 6 mg THC, 8 mg THC, 10 mg THC, 12 mg THC, 15 mg THC or 20 mg THC. Similarly, a therapeutic composition according to the present invention, which composition comprises 20 mg CBD, can be compared with that of CBD-containing extract diluted with olive oil for relieving the condition of epileptic patients. According to an embodiment, for at least some patients, relief with the therapeutic composition is greater than that found when using oil-diluted extract containing 20 mg CBD, 30 mg CBD, 40 mg CBD, 60 mg CBD, 80 mg CBD, 100 mg CBD, 120 mg CBD, 150 mg CBD or 200 mg CBD.

According to an embodiment, said therapeutic composition is characterized by a therapeutic effect, provided to at least some patients, different than that of said at least one cannabinoid. According to an embodiment, said therapeutic composition is further characterized by an effect different than that of said honey. According to an embodiment, at least one therapeutic effect provided to at least some patients by said therapeutic composition is in addition to the therapeutic effects provided by the at least one cannabinoid and honey.

According to an embodiment, said therapeutic composition has an effect, which does not exist in another preparation containing same cannabinoid or cannabinoids at same amounts(s). According to an embodiment, said therapeutic composition has an effect, which does not exist in an extract of a cannabis plant prepared so that it contains same amounts of cannabinoids as those in said therapeutic composition, and optionally same amounts of non-cannabinoid cannabis compounds. Effects of cannabinoids differ between patients of similar indications. According to an embodiment, treating patient A and patient B with the same other preparation, e.g. oil-diluted extract, at same amounts relieves conditions of patient A, but not those of patient B. According to an embodiment, said therapeutic composition, containing same amount of cannabinoids as in the other preparation relieves the conditions also of B. Additionally, particular other cannabinoids preparations, e.g. oil-diluted extract, relieve conditions related to indication A of some patients, but not those related to indication B. According to an embodiment, said therapeutic composition, containing same amount of cannabinoids as in these other preparation relieves also the conditions related to indication B.

Without wishing to be limited by theory, it is suggested that said homogeneous distribution of said cannabinoid or cannabinoids in the therapeutic composition gives room for new interactions, ones that do not exist in cannabis extract nor in honey. According to one embodiment new interactions exist between a cannabinoid or cannabinoids and at least one honey compound, e.g. a sugar or a flavonoid, which interactions modify the effect of said cannabinoid(s). According to another embodiment said new interactions exist between homogeneously distributed, non-cannabinoid cannabis compounds and at least one honey compound and such interactions modify the effect of said non-cannabinoids on cannabinoids performance. Additionally or alternatively, high viscosities in said therapeutic composition and hindered diffusion play an important role.

According to an embodiment, further provided are a digestible product and/or a topical application product comprising said therapeutic composition. According to an embodiment, said product is selected from the group consisting of emulsions, solutions in various solvents, including oils and capsules containing said therapeutic compositions. According to an embodiment, said product is selected from the group consisting of foods, food additives, animal feeds, beverages, cosmetic products, pharmaceuticals and nutraceuticals. According to an embodiment, said product is a candy or a chocolate comprising said therapeutic composition.

According to an embodiment, further provided is a method for treating a patient, comprising providing a therapeutic composition according to any of the above embodiments. According to an embodiment, said patient suffers pain. According to an embodiment, said patient is epileptic. According to an embodiment, the method further comprises providing to a patient several of said therapeutic compositions, and selecting out of those the most suitable therapeutic composition. According to an embodiment, the method further comprises providing to a patient a therapeutic compositions according to the present invention and replacing it from time to time with another therapeutic compositions according to the present invention. According to an embodiment, said providing is via the mouth, skin, a mucosal tissue or a combination thereof.

According to an embodiment, further provided is a method of producing said therapeutic composition comprising providing honey; providing a cannabis extract comprising said cannabinoid and said non-cannabinoid cannabis compounds; and blending said provided honey and said provided cannabis extract to form a blend. According to an embodiment, said method further comprises homogenizing the blended components, e.g. via applying a homogenizer.

Any honey is suitable. According to an embodiment, said honey is selected from bees honey and date honey. According to an embodiment, said honey is selected from the group consisting of eucalyptus honey, avocado honey, orange blossom honey, Manuka honey, wild-glower honey and mixtures thereof.

According to an embodiment, said honey comprises less than 24 wt % water, less than 23% wt, less than 22% wt, less than 21% wt, less than 20% wt, less than 19 wt %, less than 18% wt, less than 17% wt, less than 16% wt, less than 15% wt, less than 14% wt, less than 13% wt, less than 12% wt, less than 11% wt or less than 10% wt.

According to an embodiment, said method further comprises blending with a food-approved emulsifier. According to an embodiment, said method further comprises blending with a vegetable oil. According to an embodiment, said method further comprises blending with an antioxidant.

According to an embodiment, said method further comprises blending with a pharmaceutical composition. According to an embodiment, said food-approved emulsifier, vegetable oil, antioxidant and/or a pharmaceutical is blended with the honey prior to blending with said extract, blended with said extract prior to blending with the honey, added to the blend of honey and extract after its formation or concurrently with it or combinations thereof.

According to an embodiment, said honey comprises glucose oxidase and said method further comprises at least partial deactivation and/or denaturation of said glucose oxidase prior to said blending of simultaneously with it, e.g. via heat treatment.

According to an embodiment, said blending is conducted at a temperature under 90° C., under 80° C., under 70° C., or under 60° C. According to an embodiment, said blending is conducted at a temperature above 30° C., above 35° C., above 40° C., above 45° C., or above 50° C. According to an embodiment, said blending is conducted at a temperature between 40° C. and 50° C. According to an embodiment, at the end of the blending, the blend is brought to room temperature within 10 minutes.

According to an embodiment, the extract is blended first with a fraction of the honey to form an intermediate blend, which is then blended with the rest of the honey.

According to an embodiment, said provided cannabis extract comprises a solvent and said method further comprises removing at least a fraction of said solvent during said blending, after said blending or a combination thereof. According to an embodiment, said removing at least a fraction of said solvent is conducted at sub-atmospheric pressure.

According to an embodiment, said providing a cannabis extract comprises extracting cannabis plant material. According to an embodiment, said extracting comprises contacting said plant material with a solvent. According to an embodiment, said solvent is selected from ethanol, aqueous ethanol solutions, liquefied gas or a compound in super-critical form. According to an embodiment, said extracting comprises steam distillation. According to an embodiment, said providing a cannabis extract further comprises at least partial decarboxylation of cannabinoids in said extract. According to an embodiment, said providing a cannabis extract further comprises dewaxing said extract, e.g. via winterizing.

According to an embodiment, said providing a cannabis extract comprises enrichment in a cannabinoid, e.g. via distillation, a second extraction, crystallization and/or chromatographic separation. According to an additional embodiment, said providing a cannabis extract comprises enrichment in a non-cannabinoid cannabis compound, e.g. a terpene. According to an additional embodiment, said enrichment in a non-cannabinoid cannabis compound comprises adding at least one terpene to the extract prior to blending and/or to the blend.

According to an embodiment, said method further comprises at least one of blending under a non-oxidative atmosphere (e.g. nitrogen), using blending procedures that minimize air introduction to the blend, removing air from the blend, packaging in a container that minimizes or blocks air contact and packaging in a non-oxidative atmosphere (e.g. nitrogen). According to an embodiment, said method further comprises packaging in a dark container.

EXAMPLES

Examples 1-3: Preparing Cannabis Plant Extract

Buds of three strains are dried at ambient temperature and at controlled moisture. The dried buds are then ground and mixed well for homogenization. Moisture content is 11.2% wt. The dried and ground plant is extracted by mixing with 95% ethanol solution at 10 milliliter (ml) ethanol solution per 1 gr of plant material. Mixing is conducted at ambient temperature for 30 minutes. Then the plant material is filtered out and the solution is evaporated at sub-atmospheric pressure for removing the majority of the ethanol. The remaining solution is kept in a freezer for at least 24 hours, followed by filtering out waxes. The de-waxed solution is further evaporated for removing the rest of the ethanol. The residual solution is then kept at a temperature of 120 C until bubbling stops to form the decarboxylated extract. Samples of the extract are analyzed for their cannabinoids content. The results are summarized in Table 1:

TABLE 1

| Example | Strain (source in Israel) | CBG (% wt) | CBD (% wt) | CBN (% wt) | THC (% wt) |
|---|---|---|---|---|---|
| 1 | Cheese-Pie/CHP (Better) | | 61.1 | | 2.8 |
| 2 | Quartz (BOL) | | | 1.0 | 61.3 |
| 3 | Magen (IMC) | 1.6 | 36.1 | | 28.4 |

Examples 4-12: Preparation of Honey-Extract Compositions

Wild flower honey, eucalyptus honey, avocado honey and orange blossom honey are blended with extracts generated in Examples 1-3 or with a mixture formed by mixing Extracts 1 and 2. Optionally other ingredients are also added to the blend, tocopherol, sorbate (Tween), lecithin and/or water. In all cases, the honey is heated first to about 45° C. Then the extract and other ingredients are gradually added, while thoroughly mixing under nitrogen enriched atmosphere. Mixing is continued for 30 minutes after the addition is completed. Bubbles are allowed to release and blend is allowed to cool to room temperature and then sealed under the same atmosphere. Concentrations of various ingredients in the blend are calculated based on mixed compositions and mixing proportions. Samples are taken for analysis. Details of the various preparations are shown in Table 2.

TABLE 2

| | | | | | Calculated concentration in the blend | | | | |
|---|---|---|---|---|---|---|---|---|---|
| | | | Added ingredients | | CBD | THC | Carbohydrates | A | B |
| Example | Honey | Extract | A | B | (ppm) | (ppm) | (%) | (%) | (%) |
| 4 | Avocado | Magen | Tocopherol | | 5545 | 4360 | 79 | 0.2 | |
| 5 | Eucalyptus | CHP | Lecithin | | 355 | 15 | 81 | 0.1 | |
| 6 | Wild flowers | Quartz | Water | | 10 | 455 | 74 | 10 | |

TABLE 2-continued

| | | | Added ingredients | | Calculated concentration in the blend | | | | |
| --- | --- | --- | --- | --- | --- | --- | --- | --- | --- |
| | | | | | CBD | THC | Carbohydrates | A | B |
| Example | Honey | Extract | A | B | (ppm) | (ppm) | (%) | (%) | (%) |
| 7 | Wild flowers | CHP/ Quartz mixture | | | 1150 | 1050 | 81 | | |
| 8 | *Eucalyptus* | CHP | Tween | | 1450 | 65 | 80 | 0.2 | |
| 9 | *Eucalyptus* | Magen | Tocopherol | Tween | 180 | 140 | 79 | 0.2 | 0.3 |
| 10 | Orange blossom | CHP/ Quartz mixture | | | 75 | 65 | 81 | | |
| 11 | Orange blossom | Quartz | Lecithin | | 10 | 580 | 80 | 0.1 | |
| 12 | Avocado | CHP | Tocopherol | Lecithin | 2430 | 110 | 80 | 0.3 | 0.2 |
| Comparative | Wild flowers | CHP/ Quartz mixture | Water | | 860 | 790 | 62 | 33 | |

Analysis: Honeys formed according to several of the examples in Table 2 are analyzed (in triplicates) at several times after preparation, and cannabinoids oxidation after a month are calculated. The results are presented in Table 3.

TABLE 3

| | Oxidation after a month (%) | |
| --- | --- | --- |
| Example | THC | CBD |
| 5 | <3% | <3% |
| 6 | 17 | |
| 7 | <3% | <3% |
| 8 | <3% | <3% |
| Comparative | 45 | 62 |

The invention claimed is:

1. A therapeutic composition providing therapeutic effects to at least some patients comprising,
 (i) honey;
 (ii) at least one cannabinoid; and
 (iii) optionally, at least two non-cannabinoid cannabis compounds, hydrogen peroxide, at least one food-approved antioxidant, glucose oxidase, and/or catalase, and
 (iv) water at a concentration of less than 26% by weight; wherein the composition is characterized by two or more of:
 (a) being homogeneous;
 (b) having oxidative power low enough to keep tetrahydrocannabinol oxidation at a rate of less than 20% per month;
 (c) containing hydrogen peroxide at a concentration low enough to keep tetrahydrocannabinol oxidation at a rate of less than 20% per month;
 (d) containing at least one food-approved antioxidant at a concentration low enough to keep THC oxidation at a rate of less than 20% per month;
 (e) containing glucose oxidase at a concentration low enough to keep tetrahydrocannabinol oxidation at a rate of less than 20% per month; and/or
 (f) containing catalase at a concentration high enough to keep tetrahydrocannabinol oxidation at a rate of less than 20% per month.

2. The therapeutic, composition of claim 1, additionally characterized by at least two of (a) to (f).

3. The therapeutic composition of claim 1, additionally characterized by at least three of (a) to (f).

4. The therapeutic composition of claim 1, additionally characterized by at least four of (a) to (f).

5. The therapeutic composition of claim 1, additionally characterized by (a) and at least one of (b) to (f), at least two of (b) to (f) or at least three of (b) to (f).

6. The therapeutic composition of claim 1, containing at least two non-cannabinoid cannabis compounds, wherein at least one of said non-cannabinoid cannabis compound is selected from the group consisting of terpenes, terpenoids and flavonoids.

7. The therapeutic composition of claim 1, wherein the concentration of cannabinoid in the composition is less than 10% by weight.

8. The therapeutic composition of claim 1, wherein the concentration of cannabinoid in the composition is greater than 10 parts per million of total component parts present in the composition.

9. The therapeutic composition of claim 1, wherein said cannabinoid comprises cannabidiol and tetrahydrocannabinol in a weight ratio of cannabidiol to tetrahydrocannabinol greater than 5.

10. The therapeutic composition of claim 1, wherein at least one therapeutic effect provided to at least some patients is greater than that provided by the at least one cannabinoid.

11. The therapeutic composition of claim 1 wherein at least one therapeutic effect provided to at least some patients is in addition to the therapeutic effects provided by the at least one cannabinoid and honey.

12. A digestible product containing the therapeutic composition of claim 1.

13. A topical application product containing the therapeutic composition of claim 1.

* * * * *